United States Patent [19]

Virgilio et al.

[11] Patent Number: 4,477,683
[45] Date of Patent: Oct. 16, 1984

[54] 3-METHYL-1-(2,2,4-AND 2,4,4-TRIMETHYL-1-CYCLOPENTYLIDENE) PENT-2-EN-4-ONE AND ISOMERS, AND PERFUME COMPOSITIONS THEREOF

[75] Inventors: Joseph A. Virgilio, Wayne; Emanuel Heilweil, Fairfield, both of N.J.

[73] Assignee: Givaudan Corporation, Clifton, N.J.

[21] Appl. No.: 374,368

[22] Filed: May 3, 1982

[51] Int. Cl.$^3$ ............................................. C07C 49/21
[52] U.S. Cl. .................................... 568/379; 568/443; 568/446; 252/522 R
[58] Field of Search ................................ 568/379, 446

[56] References Cited

U.S. PATENT DOCUMENTS

| 2,815,378 | 12/1957 | Klein | 568/446 |
| 2,870,208 | 1/1959 | Guex et al. | 568/379 |
| 3,963,675 | 6/1976 | Noegeli | 568/446 |
| 4,052,341 | 10/1977 | Naipawer et al. | 568/379 |
| 4,173,584 | 11/1979 | Dastin | 568/379 |
| 4,173,585 | 11/1979 | Yoshida et al. | 568/379 |

FOREIGN PATENT DOCUMENTS

| 2601144 | 7/1977 | Fed. Rep. of Germany | 568/379 |
| 1204407 | 1/1960 | France | 568/379 |

OTHER PUBLICATIONS

Easter et al., Chem. Abst., vol. 93, #149961S, (1980).
Slomp et al., J. Org. Chem., vol. 25, pp. 514–518, (1960).
Wasson et al., Org. Syn., vol. 37, pp. 58–59, (1957).
Ryerson et al., Org. Syn., vol. 39, pp. 70–72, (1959).
Vrehe, "Chem. of Acetylenes", Marcel Dekker, N.Y., pp. 207–219, (1969).
Pauling et al., Helv. Chim. Acta., vol. 59, pp. 1233–1243, (1976).

Primary Examiner—James H. Reamer
Attorney, Agent, or Firm—Robert F. Tavares

[57] ABSTRACT

There is provided novel ketones of the structure:

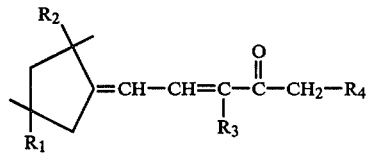

wherein:
$R_1$, $R_2$, $R_3$ and $R_4$ represent hydrogen or methyl provided that:
$R_1$ is not the same as $R_2$ and
$R_3$ is not the same as $R_4$;
and fragrance compositions containing them.

5 Claims, No Drawings

3-METHYL-1-(2,3,4-AND 2,4,4-TRIMETHYL-1-CYCLOPENTYLIDENE) PENT-2-EN-4-ONE AND ISOMERS, AND PERFUME COMPOSITIONS THEREOF

THE INVENTION

This invention provides novel odorant ketones of the formula

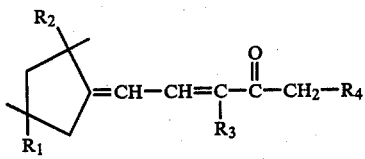

wherein:

$R_1$, $R_2$, $R_3$ and $R_4$ represent hydrogen or methyl, provided that $R_1$ is not the same as $R_2$, and $R_3$ is not the same as $R_4$.

The ketones represented by formula I can be prepared via the novel sequence of steps illustrated below.

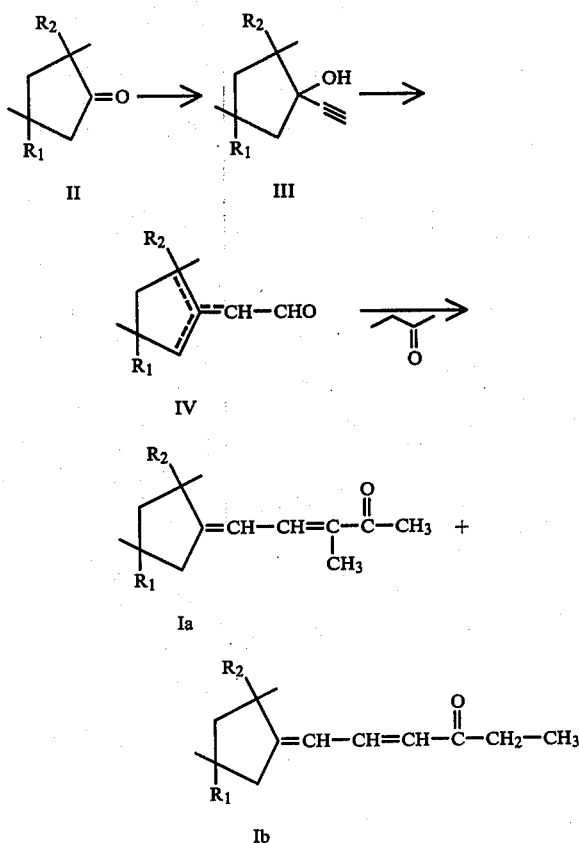

In this process the ketone II is reacted with an alkali metal acetylide to form the ethynyl alcohol III which is then rearranged to the aldehyde IV. Reaction of aldehyde IV with 2-butanone results in a mixture of the isomers Ia and Ib, which are compounds of formula I wherein $R_3$ is $CH_3$ and $R_4$ is H (Ia) and wherein $R_3$ is H and $R_4$ is $CH_3$ (Ib) respectively.

The compounds represented by formula I have precious woody notes, which make them valuable in fragrance formulations.

DESCRIPTION OF THE PREFERRED EMBODIMENTS

As indicated above, the first step in the novel process involves reacting the trimethylcyclopentanone II with an alkali metal acetylide to form the ethynyl alcohol III. The starting ketone may be either the pure isomers IIa ($R_1$=hydrogen) or IIb ($R_2$=hydrogen) or a mixture thereof. It is preferred, on economical grounds, to use the commercially available mixture which consists of about 60% IIa and 40% IIb. Both IIa and IIb can be prepared in pure form by the method described in J. Org. Chem. 25 514 (1960). Pure IIb can also be prepared by the methods described in Org. Syn. 39 70 (1959) and Org. Syn. 37 58 (1957).

The ketone II can be converted to the corresponding ethynyl alcohol III with an alkali metal acetylide. Methods for reacting ketones with alkali metal acetylides to form ethynyl alcohols are well known in the art. (See for example Heinz Günter Viehe, *Chemistry of Acetylenes* Chapter 3, Marcel Dekker, New York, 1969 wherein a number of such methods are described). The better known methods utilizing sodium acetylide in ammonia, lithium acetylide ethylene diamine complex, KOH and acetylene in an organic solvent, etc. are preferred.

The rearrangement of ethynyl alcohols to unsaturated aldehydes are well known in the art. Acid catalyzed rearrangements, e.g. the Meyer-Schuster rearrangement, have been reported, many of which lead to a complex mixture of products. Better yields are obtained by rearranging esterified ethynyl alcohols in the presence of certain transition metals or by the direct rearrangement of the ethynyl alcohol in the presence of silated vanadates.

The preferred method for effecting this rearrangement is similar to the one reported by Pauling et al., Helv. Chem. Acta, 59, 1233 (1976) wherein a tris [trialkylsilyl or triarylsilyl] vanadate is used, the tris-(triphenylsilyl) vanadate being especially preferred. The preferred amount of catalyst to ethynyl alcohol is about 0.01 to 0.1 moles/mole with about 0.03 to 0.04 being especially preferred. Hydrocarbons, ethers and mineral oil are suitable solvents. Temperatures between 100° and 150° are preferred with 130° C. to 145° C. being especially preferred. The use of excess triphenylsilanol and a carboxylic acid, such as benzoic acid, to inhibit dehydration is also preferred.

The condensation of the resulting aldehyde with 2-butanone may be accomplished by methods similar to those known in the art for the condensation of ketones with aldehydes in an aldol-type reaction. It is preferred to use a strong base such as aqueous-methanolic potassium hydroxide solution and to use an excess of the more economical ketone. In the preferred process, the reaction is run from 10 to 48 hrs at −15° to 5° C. followed by a similar period at 15° to 40° C. It is especially preferred to use a reaction time of 20–28 hrs at −15° to 5° followed by a similar period at 25°–30°. An isomeric mixture of ketones of structure I is obtained which is about 70 to 90% of structure Ia, 3-methyl-1-(2,2,4- and 2,4,4-trimethyl-1-cyclopentylidene)pent-2-en-4-one, and about 30 to 10% of structure Ib, 1-(2,2,4- and 2,4,4-trimethyl-1-cyclopentylidene)hex-2-en-4-one. Ketones Ia and Ib may be separated by distillation e.g. on a spinning-band distillation apparatus.

The pure Ia has an odor which is described as woody, ionone and fruity in nature. The compound is particularly valuable in precious wood-type fragrance bases, such as, vetiver, sandalwood, etc., because of the ability to enhance the desired precious woody character and to add body or fullness to the composition.

It is preferred, however, to use the mixture obtained in the condensation reaction which contains from ten to thirty percent Ib, usually about 20%. This mixture has the same precious woody notes as the pure Ia with suggestion of olibanum and buttery notes and the mixture can be used in most all compositions where the pure Ia is used. In some compositions the additional spicy character of the mixture is used to good effect. For example, when added to an amber composition, the mixture of 80% Ia and 20% Ib was found to blend the citrus notes, animal notes and sweet notes while adding desirable spicy notes to provide a more desirable, well rounded, spicy, amber composition.

The novel ketones of the invention can be used in perfume formulations in a practical range extending from about 0.1 to 20% depending on the type of formulation involved. Concentrations above 20% may be used for special effects.

The novel ketones of this invention can be used to prepare odorant compositions which can be used as odorant bases for the preparation of perfumes and toilet waters by adding the usual alcoholic and aqueous diluents thereto: approximately 15-20% by weight of base would be used for perfumes and approximately 3-5% by weight would be used for toilet waters.

Similarly, the base compositions can be used to odorize soaps, detergents, cosmetics, or the like. In these instances, a base concentration of from about 0.5 to about 2% by weight can be used.

ILLUSTRATION OF THE PREFERRED EMBODIMENTS

The following examples are used to illustrate the preferred embodiments of this invention as it is now preferred to practice it. It will be understood that such examples are merely illustrative and the invention is to be limited thereto only as indicated in the claims. Perfume ingredients are given in parts/thousand and weight in grams. Where the material used is better known by its common name, tradename or trademark, such a name is used with the chemical name being given in parenthesis.

Chemical analysis, where given in the examples, were conducted in the following manner. Mass spectral analyses were done on a Finnigan Model 4000 instrument; mass numbers in m/e. Nuclear magnetic spectra were recorded as solutions in chloroform-$d_1$ on a Varian Model EM 360L spectrometer and are reported as $\delta$ units relative to tetramethylsilane (TMS) (0.0 $\delta$). Gas-liquid chromatography was conducted on a Hewlett-Packard Model 5880A gas chromatograph on a 0.25 mm×12 mm. Carbowax 20M, fused silica capillary column. Infrared spectra were recorded as neat samples on a Perkin-Elmer Model 457 and absorptions are reported in inverse centimeters.

EXAMPLE I

Preparation of 3-Methyl-1-(2,2,4- and 2,4,4-trimethyl-1-cyclopentylidene)pent-2-en-4-one, Ia (A) A mixture of n-butanol (105 ml) and powdered potassium hydroxide (600 g) in dry toluene (1400 ml) was heated under a nitrogen blanket at 100° C. for 30 minutes. The mixture was cooled to −5° C., and dimethylformamide (100 ml) was added. Acetylene (gas) and a solution of 2,2,4- and 2,4,4-trimethylcyclopentanone (315 g) in dry toluene (338 ml) were introduced simultaneously over a period of 2 hrs. The acetylene addition was continued for an additional 3 hrs. After displacing unreacted acetylene with nitrogen and quenching the reaction mixture on water (1300 ml), the toluene layer was separated, washed with 5% $NaHCO_3$ (500 ml) and concentrated to yield 264 g of an oil.

This procedure was repeated three times. The resultant combined oil yielded, upon distillation, 467 g of ethynyl alcohol, III; b.p: 87°-90° C. @ 26 mm Hg.

(B) To a mixture of 47.5 g (0.17 m) triphenylsilanol, 22.4 g (0.025 m) tris (triphenylsilyl) vanadate and 2.2 g benzoic acid in 1587 ml of mineral oil was added 100 g (0.68 m) of the ethynyl-alcohol from (A). The mixture was heated at 140° for 7 hrs followed by flash distillation of the crude product. Three distillates were prepared in a similar manner by recycling of the catalyst system. A total crude of 173 g was distilled at 10 mm Hg. The distillation was followed by gas chromatography. The fractions distilling from 80°-102° were combined to yield 145 g of product; H-nmr; 10.09$\delta$ and 9.80 (2d, $\alpha,\beta$-unsat. C=O), 9.43 to 9.60 (multi, $\beta,\gamma$-unsat. C=O).

(C) A solution of 10.1 g potassium hydroxide, 123 g water and 340 g methanol was cooled to 5° C. There was added 145.5 g 2-butanone. The aldehyde obtained from step B (50 g) was then added over a 25 minute period, at ±5° C. The mixture was stirred for ½ hr, and then held for 24 hrs at 0°-5° and an additional 24 hrs at 25°. The mixture was clarified with 12.3 g of 62.5% $H_2SO_4$ and the pH was adjusted to 6 with 20% NaOH. The light components were removed by atmospheric distillation to a temperature of 100°. The residue, 63.2 g, was washed neutral and distilled at 2.0 mm Hg. The distillation was followed by gas chromatographic analysis. The fractions distilling at 113°-118° were combined to yield 38 g of product containing 96% of two components present at a ratio of 82:18. The two components were identified by gas chromatographic mass-spectral analysis as being the two possible structural isomers; 3-methyl-1-(2,2,4- and 2,4,4-trimethyl-1-cyclopentylidene)pent-2-en-4-one (Ia) and 1-(2,2,4- and 2,4,4-trimethyl-1-cyclopentylidene) hex-2-en-4-one (Ib); MS (m/e) analysis: Ia: (206) molecular weight (163) loss of $CH_3C$=O (43) $CH_3C$=O; Ib: (206) molecular weight (149) loss of $CH_3CH_2C$=O (57) $CH_3CH_2C$=O.

Odor: woody, olibanum, buttery, Immortelle.

(D) The product composition in (C) was further rectified by spinning band distillation at 0.9 mm Hg on a Nester-Faust NFA 100 Auto-Annular Still. Compound Ia was separated as substantially pure; b.p.: 89°-90° C.: molecular weight 206; ir: 1670 (s), 1637 (s); H-nmr: 108 $\delta$ (3H,s) and 1.20 (3H,s, geminal dimethyl group), 1.08 (3H, d, J=5.5 Hz), 1.87 (3H, s, olefinic $CH_3$), 2.33 (3H,s, acetyl $CH_3$), 6.13 [1H, d, (J=12)+t, (J=2), $\gamma$-H of dienone system] and 7.20 (1H, d, J=12 Hz, $\beta$-H of dienone system).

Odor: woody, ionone, fruity.

EXAMPLE II

The use of ketone Ia in a vetiver base.

| Vetiver Base | |
|---|---|
| Components | Parts |
| Vetiver Oil Bourbon | 290 |
| Santalol | 200 |
| Laurine ® (hydroxycitronellal) | 90 |
| Cinnamic Alcohol | 50 |
| Heliotropin | 60 |
| Coumarin | 30 |
| Musk Ketone (4-t-Butyl-3,5-dinitro-2,6-dimethylacetophenone) | 50 |
| Musk Ambrette (6-t-butyl-3-methyl-2,4-dinitroanisole) | 30 |
| Propylene Glycol | 100 |
| | 900 |

The addition of 100 parts of ketone Ia to the vetiver base fills out the body of the composition while enhancing the precious woody notes.

EXAMPLE III

Use of ketone I in an amber base.

| Amber Base | |
|---|---|
| Components | Parts |
| Labdanum Resin Soluble | 376.3 |
| Patchouli Moyenne | 19.8 |
| Benzoin Soluble Resin | 99.0 |
| Vetiver Bourbon | 49.5 |
| Sandalwood E.I. | 99.0 |
| Mousse de Chene Absolute (50% in ethanol) | 19.8 |
| Musk Ambrette (6-t-Butyl-3-methyl-2,4-dinitroanisole) | 49.5 |
| Musk Ketone (4-t-Butyl-3,5-dinitro-2,6-dimethylacetophenone) | 49.5 |
| Vanillin USP | 49.5 |
| Bergamot N.S. | 69.3 |

| -continued | |
|---|---|
| Amber Base | |
| Components | Parts |
| Orange California C.P. | 49.5 |
| Rose 392/2 (Givaudan Specialty Base) | 49.5 |
| Castoreum Absolute (10% in ethanol) | 9.9 |
| | 990.1 |

The addition of 9.9 parts of the ketone mixture I, as obtained in Example I (C), has a noticeable effect on the amber base. Before the addition of I, the composition exhibits slightly discordant notes of a citrus, animal and sweet nature. The addition of I has the effect of blending these notes and adds a spicy character resulting in a more desirable amber blend.

We claim:

1. A compound of the formula

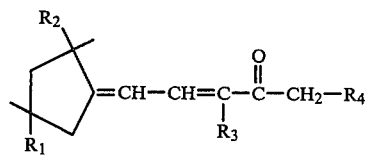

wherein:
$R_1$, $R_2$, $R_3$ and $R_4$ represent hydrogen or methyl provided that
$R_1$ is not the same as $R_2$ and
$R_3$ is not the same as $R_4$.

2. A compound according to claim 1 wherein $R_4$ is hydrogen.

3. A compound according to claim 2 wherein $R_2$ is hydrogen.

4. A compound according to claim 2 wherein $R_2$ is methyl.

5. A compound according to claim 1 which is a mixture of isomers wherein 90 to 70% are isomers wherein $R_4$ is hydrogen and 10 to 30% are isomers wherein $R_4$ is methyl.

* * * * *